United States Patent
Nawasrah (10) Patent No.: US 10,076,471 B2
(45) Date of Patent: Sep. 18, 2018

(54) ANTIMICROBIAL DENTURE

(71) Applicant: University of Dammam, Dammam (SA)

(72) Inventor: Amal M. Nawasrah, Dammam (SA)

(73) Assignee: University of Dammam, Dammam (SA)

( * ) Notice: Subject to any disclaimer, the term of this patent is extended or adjusted under 35 U.S.C. 154(b) by 119 days.

(21) Appl. No.: 15/192,512

(22) Filed: Jun. 24, 2016

(65) Prior Publication Data

US 2017/0367934 A1 Dec. 28, 2017

(51) Int. Cl.
*A61K 6/083* (2006.01)
*A61K 6/00* (2006.01)

(52) U.S. Cl.
CPC ............ *A61K 6/0067* (2013.01); *A61K 6/007* (2013.01); *A61K 6/0008* (2013.01); *A61K 6/0017* (2013.01); *A61K 6/083* (2013.01)

(58) Field of Classification Search
None
See application file for complete search history.

(56) References Cited

U.S. PATENT DOCUMENTS

| | | | | |
|---|---|---|---|---|
| 3,169,880 A | * | 2/1965 | Strauss | B41M 5/10 106/31.69 |
| 3,255,018 A | * | 6/1966 | Comollo | A23G 4/06 106/162.8 |
| 3,507,822 A | * | 4/1970 | Miyami | A61K 6/083 424/650 |
| 4,591,384 A | * | 5/1986 | Akahane | A61K 6/033 106/35 |
| 4,925,660 A | * | 5/1990 | Atsuta | A61K 9/0063 424/78.05 |
| 5,084,491 A | * | 1/1992 | Kerby | A61K 6/0023 523/115 |
| 5,449,715 A | * | 9/1995 | Plochocka | C08K 3/30 524/284 |

FOREIGN PATENT DOCUMENTS

| | | |
|---|---|---|
| SU | 900843 B | 1/1982 |
| WO | 2006/033162 A1 | 3/2006 |
| WO | 2012/167920 A1 | 12/2012 |
| WO | 2013/059745 A1 | 4/2013 |

OTHER PUBLICATIONS

Motalebi, A., et al., "Improvement of Corrosion Performance of 316L Stainless Steel via PVTMS/Henna Thin Film", Progress in Natural Science: Materials International, vol. 22, No. 5, pp. 392-400 (Nov. 10, 2012).

* cited by examiner

*Primary Examiner* — Peter A Salamon
(74) *Attorney, Agent, or Firm* — Oblon, McClelland, Maier & Neustadt, L.L.P.

(57) ABSTRACT

A denture containing a henna powder or a henna extract, each of which comes from pulverized henna leaves and may include any of lawsone, tannic acid, and 2-methoxy-1,4-napthoquinone and a denture fabrication material. A denture containing at least one first antimicrobial ingredient selected from the group consisting of henna powder or a henna extract, lawsone, tannic acid, and 2-methoxy-1,4-napthoquinone, and a second antimicrobial ingredient, and optionally, a biocompatible gel and an odor neutralizer.

16 Claims, 2 Drawing Sheets

ANTIMICROBIAL DENTURE

BACKGROUND OF THE INVENTION

Technical Field

The present invention relates to a denture and a denture coating composition that includes an antimicrobial ingredient from henna to prevent the growth of the microbes related to denture stomatitis.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

One of the difficulties encountered during dental care is the treatment of denture stomatitis. This prevalent and long-standing problem is common in the elderly wearing complete or partial dentures. See Pattanaik, S. (2010) "Denture Stomatitis: A Literature Review," Journal of Indian Academy of Oral Medicine and Radiology, 22, 136, incorporated herein by reference in its entirety. Other studies have evaluated recurring denture stomatitis and the disease's impact on both dentist and patient. See Jeganathan, S. (1992), "Denture stomatitis—a review of the etiology, diagnosis and management," Australian dental journal, 37, 107-114, incorporated herein by reference in its entirety.

The material used to construct the denture is acrylic resin which has acceptable physical, mechanical and esthetic properties. This material suffers from the defect of allowing the adhesion of microbes which in turn allows for microbial colonization. See Jain, D., & Shakya, P. (2013). "An in vitro study on effect of Delmopinol application on *Candida albicans* adherence on heat cured denture base acrylic resin: a thorough study," Indian Journal of Dental Research, 24(5), 645; Radford, D. R. Sweet, S. P., Challacombe, S. J., & Walter, J. D. (1998). "Adherence of *Candida albicans* to denture-base materials with different surface finishes," Journal of dentistry, 26(7), 577-583; and Jafari, A. A., Fallah-Tafti, A., Fattahi-bafghi, A., & Arzy, B. (2014). "The Comparison of Predominant Oral Micro-Flora in Subjects with and without Complete Denture Referred to Yazd Dentistry Department," Journal of Community Health Research, 3(3), 195-203, incorporated herein by reference in their entirety. The adhesion of microbes to the acrylic resin is dependent on the surface properties of acrylic resin. See Pereira-Cenci, T., Del Bel Cury, A. A., Crielaard, W., & Ten Cate, J. M. (2008). "Development of *Candida*-associated denture stomatitis: new insights," Journal of applied oral science, 16(2), 86-94, each incorporated herein by reference in its entirety.

Denture-related stomatitis (DRS) is considered as the most common form of oral candidosis. See Webb, B. C., Thomas, C. J., Willcox, M. D. P., Harty, D. W. S., & Knox, K. W. (1998), "*Candida*-associated denture stomatitis. Aetiology and management: A review: Part 1. Factors influencing distribution of *candida* species in the oral cavity" Australian dental journal, 43(1), 45-50; Webb, B. C., Thomas, C. J., Willcox, M. D. P., Harty, D. W. S., & Knox, K. W. (1998), "*Candida*-associated denture stomatitis. Aetiology and management: A review. Part 2. Oral diseases caused by *candida* species" Australian dental journal, 43(3), 160-166; Webb, B. C., Thomas, C. J., Willcox, M. D. P., Harty, D. W. S., & Knox, K. W. (1998), "*Candida*-associated denture stomatitis. Aetiology and management: A review. Part 3. Treatment of oral candidosis." Australian dental journal, 43(4), 244-249, each incorporated herein by reference in their entirety. Denture stomatitis was defined as "an inflammatory process of the mucosa underlying a removable, partial or total, denture prosthesis or appliance." The international consensus eliminated lesions with known causes such as allergies to denture materials, and burns related to direct relining of the prosthesis in the mouth. See Figueiral, M. H., Azul, A., Pinto, E., Fonseca, P. A., Branco, F. M., & Scully, C. (2007), "Denture-related stomatitis: identification of aetiological and predisposing factors—a large cohort" Journal of oral rehabilitation, 34(6), 448-455, incorporated herein by reference in its entirety.

Another definition of Denture stomatitis indicates an inflammatory state of the denture bearing mucosa. Denture stomatitis is also known as denture-induced stomatitis, denture sore mouth, inflammatory papillary hyperplasia and chronic atrophic candidiasis.

The prevalence of denture stomatitis is high in denture users as reported by studies. See Kossioni, A. E. (2011) "The prevalence of denture stomatitis and its predisposing conditions in an older Greek population." Gerodontology, 28(2), 85-90, incorporated herein by reference in its entirety. A review reported DS in 11-67% of complete denture wearers. It is more common on the palatal mucosa, and affects females more. See Arendorf, T. M., & Walker, D. M. (1987), "Denture stomatitis: a review. Journal of oral rehabilitation," 14(3), 217-227, incorporated herein by reference in its entirety.

Denture stomatitis has multi-factorial etiology. Different studies reported that the risk factors, or the etiological factors of DS, include prosthetic factors and infective factors, the prosthetic factors seem to play mainly a traumatic role in its pathogenicity, such as duration of wearing a dental prosthesis, reduced vertical dimension, unstable occlusion, older prostheses and continuous wearing of a prosthesis. The most important risk factor was the continuous use of the denture. Continuous wear of the denture especially at night will minimize the defensive effect of saliva, cleaning action of the tongue, and good oxygenation of the mucosa, which affect the resistance of mucosal tissue to mechanical and microbiological aggression. Whereas Nyquist found that trauma caused by dentures was the foremost factor in denture stomatitis. See Nyquist, G. (1953), "The influence of denture hygiene and the bacterial flora on the condition of the oral mucosa in full denture cases," Acta Odontologica Scandinavica, 11(1), 24-60, incorporated herein by reference in its entirety. Denture lining materials, such as tissue conditioners, soft denture liners were associated with *Candida* growth. Surface texture and permeability of denture base also allow the adherence of the *Candida Albicans* particularly due to the rough denture surface. Although one study found no significant relationship between denture stomatitis and classic risk factors such as sex, age, hygienic habits, denture cleanliness, and the presence of *Candida* species.

The infective factors include other bacteria, but *Candida* spp., mainly *Candida albicans*, is the most common infective factor in DRS. See Zomorodian, K., Haghighi, N. N., Rajaee, N., Pakshir, K., Tarazooie, B., Vojdani, M., . . . & Vosoghi, M. (2011), "Assessment of *Candida* species colonization and denture-related stomatitis in complete denture wearers" Medical mycology, 49(2), 208-211; Pires, F. R., Santos, E. B. D., Bonan, P. R. F., De Almeida, O. P., &

Lopes, M. A. (2002), "Denture stomatitis and salivary *Candida* in Brazilian edentulous patients" Journal of oral rehabilitation, 29(11), 1115-1119; and Ramage, G., Tomsett, K., Wickes, B. L., López-Ribot, J. L., & Redding, S. W. (2004), "Denture stomatitis: a role for *Candida* biofilms" Oral Surgery, Oral Medicine, Oral Pathology, Oral Radiology, and Endodontology, 98(1), 53-59, each incorporated herein by reference in their entirety. Cawson mentioned that trauma and *candida* infection are major reasons of denture stomatitis. See Cawson, R. A. (1965). Symposium on denture sore mouth. II. "The role of *Candida*. The Dental practitioner and dental record" 16(4), 138, incorporated herein by reference in its entirety.

Certain systemic conditions such as diabetes mellitus, nutritional deficiencies (iron, folate, vitamin B12), hypothyroidism, immunocompromised conditions (HIV infection), malignancies (acute leukemia, agranulocytosis), iatrogenic immunosuppressive drugs, e.g. corticosteroids, tobacco, alcohol, hyposalivation and decrease of saliva pH are factors which appear to predispose a subject to the infective pathology. Hematological disorders also play a part in this process.

The diagnosis of denture stomatitis is as follows, determined by Newton (1962) classification: Type 1—Local inflammation as red erythematosus usually around the minor palatal salivary glands. It was thought to be related to dentures trauma. Type 2—diffuse reddening or diffuse hyperemic, smooth and atrophic mucosa extending over the entire denture area and was related to increased growth of yeasts. Type 3—Granulated or hyperemic mucosa with a nodular appearance in the center of the palate and it was related to both trauma and *Candida* infection.

The patient is usually unaware of the condition as it is a chronic symptom-free disease, unless accidentally detecting the abnormality in the patient's palate or on regular checkup. Often detection on the palate occurs at a late stage of the infection.

The etiology is multifactoral thus the management is complex and study conclusions vary with respect to different treatment regimens. Exemplary treatments involve correction of ill-fitting dentures, antiseptics, disinfecting agents and plaque control. One study mentioned that sufficient treatment in most cases of denture stomatitis includes elimination of denture faults, denture hygiene and cessation of denture wear for a duration of time without the use of antiseptic or antimycotic drugs routinely.

Another study found that topical antifungal agents such as nystatin and amphotericin B are effective initially, and to control dental plaque the patient should use antiseptics and disinfecting agents as they play a great role in that. Also, using sodium hypochlorite to soak the denture at night will reduce denture plaque. Other investigations have shown that microwave irradiation of dentures at a specified setting and exposure time is bactericidal and candidacidal.

One approach to treatment of denture-related stomatitis is antifungal agents. Antifungal agents act by inhibiting pathways of enzymes, substrates, or transport of enzymes and substrates which are necessary for cell membrane synthesis or altering the permeability of the cell membrane of the fungal cell. It may also alter RNA and DNA metabolism or an intracellular accumulation of peroxide that is toxic to the fungal cell.

Amphotericin B is an effective topical agent as a topical lotion applied topically twice daily, and it is the drug of choice for intravenous treatment of lethal *Candida* infections. Nystatin is used as a topical agent in oral and pharyngeal candidosis, in a form of a suspension 100,000 unit per ml, without being absorbed when ingested through the gastrointestinal tract. One study reported that both amphotericin B and nystatin have an unpleasant taste, with some side effects in the gastrointestinal tract such as nausea, vomiting and diarrhea when used orally. This study also found that the broad-spectrum antifungal agents includes imidazole compounds such as clotrimazole, miconazole, econazole and ketoconazole, affect permeability of *Candida* membrane by interfering with the synthesis of ergosterol; they also bind more strongly to *Candida* enzymes than to mammalian enzymes. Clotrimazole (1% cream) is only used topically, because of gastrointestinal and neurological toxicity. Econazole exists in topical form only; miconazole (2-4% cream) and ketoconazole (200-400 mg, orally once daily) can be used both topically and systemically.

One study tested the efficacy of denture lining materials containing antifungals in the treatment of denture stomatitis, which confirmed the inhibitory effect of tissue conditioners incorporated with nystatin. While others found that the addition of nystatin powder to tissue conditioner was successful in inhibiting the growth of *Candida albicans, Candida tropicalis,* and *Candida krusei.*

In his review in 1998, Webb et. al. found that the effect of the antifungal agent depends on its concentration, susceptibility of the strain and the source of the mucosal surface. The treatment of denture stomatitis can be cost-prohibitive and prolonged with high chance of recurrence, due to the nature of the fungal infection.

The presence of a device or a prosthesis inside the patient body, such as intraoral dentures, can become a site for growth of *candida* organisms in a form of mono- or multi-species biofilms. These biofilms are reservoirs of infection and allow the organisms to spread to distant sites or cause local disease by destroying the nearby tissue surfaces with their metabolic products and enzymes. See Coogan, M. M., Fidel, P. L., Komesu, M. C., Maeda, N., & Samaranayake, L. P. (2006) (B1) "*Candida* and mycotic infections" Advances in dental research, 19(1), 130-138, incorporated herein by reference in its entirety. *C. albicans* adhere to the oral surfaces such as oral mucosa and acrylic dentures with complex interactions through hydrostatic and electronic forces and these forces are affected by many factors such as saliva, pH, bacteria and hyphal formation.

*C. albicans* yeast cells or blastospores are unicellular, eukaryotic organisms, which multiply by budding. When the bud reaches the optimal size, nuclear division occurs with a septum between the two cell units. Different studies described hypha as a microscopic tube containing multiple cell units divided by septa and may arise from existing hyphae or from blastospores. Pseudohypha is formed when blastospores are produced one from another in linear fashion without separating. True separate hyphae are produced mainly by *C. albicans*. The entire candidal cellular aggregate including hyphae, branches and lateral buds are referred to as a mycelium.

*Candida* species form soft cream-colored colonies with a yeasty odor when grown under aerobic conditions on medium which has a pH in the range of 2.5-7.5, and a temperature in the range of 20°-38° C., Growth is usually detected in 48-72 hours. The ability of yeasts to grow at 37° C. is an important characteristic to be considered in their identification from clinical specimens as most pathogenic species grow readily at 25° C. and 37° C.

The gross microscopic appearance of all the species is similar in that all yeasts are Gram-positive, but sometimes the shapes of the blastospores can vary from ovoid to elongated or spherical. Microscopically, *C. albicans* exhibits dimorphism in which there is a transition from ovoid budding blastospores (yeast cells) to parallel-sided hyphae. Size also varies, with measurements for *C. albicans* and *C. krusei* blastospores being given as 2.9-7.2, 2.9-14.4 µm and 2.2-5.6, 4.3-15.2 µm respectively.

The production of pseudohyphae is one of the major differences between *C. glabrata* (a species that cannot form pseudohyphae) and other medically important *candida* species. Observation of germ tubes and chlamydospores (large thick-walled cells which develop at the tips of pseudohyphae) are also helpful in identifying *C. albicans*.

*C. albicans* is the most common of the *candida* species found within the oral cavity. *Candida* organisms, as commensal members of the normal oral microbiota, form 40 percent (20-60 percent range) in the human population. The first oral source of *C. albicans* is the dorsum of the tongue while mucosa and plaque-covered tooth surfaces are colonized secondarily. However, with immunosuppressed persons *C. albicans* infection causes candidosis, which could be superficial, involving the mucosa, or disseminated, which is an invasive more serious form.

Saliva reduces the adhesion of *C. albicans* to acrylic resin, whereas serum, which may enter the oral cavity as a result of trauma to the palatal mucosa, enhances adhesion. Some studies mentioned that salivary proteins or mucin act as receptors for manno-proteins on the surface of *C. albicans*.

One study reported that colonization of *candida* species favors an acidic environment. Contrary findings indicate a relationship between low pH levels and denture plaque obtained from upper dentures of denture stomatitis patients on sucrose or glucose-rich diets.

Webb presented data that bacteria may further contribute to the colonization and proliferation of *candida* strains in the oral cavity. Many investigators agreed that the hyphal form of *C. albicans* is associated with its invasiveness. As there was strong correlation between germ tube formation and increased adhesion of *C. albicans* to human mucosa cells.

Antifungal agents can produce side effects in some patients, and the condition can recur if the drug is stopped. Kuhn in 2002 mentioned that the problem encountered with treating, *C. albicans* is enhancing resistance to antimicrobials and decreasing susceptibility to a variety of antifungal agents including fluconazole, nystatin, chlorhexidine, terbenafine, amphotericinB, and the triazolesvoriconazole and ravuconazole. See Kuhn, D. M., George, T., Chandra, J., Mukherjee, P. K., & Ghannourn, M. A. (2002), "Antifungal susceptibility of *Candida* biofilms: unique efficacy of amphotericin B lipid formulations and echinocandins" Antimicrobial agents and chemotherapy, 46(6), 1773-1780; and Coogan, M. M., Fidel, P. L., Komesu, M. C., Maeda, N. & Samaranayake, L. P. (2006), (B1) "*Candida* and mycotic infections" Advances in dental research, 19(1), 130-138, each incorporated herein by reference in their entirety.

Evidence, as presented above, indicates that antifungal agents are associated with a variety of problems including antifungal resistance, toxicity and the long duration of treatment. A more effective anti-fungal agent which is not prone to the same issues as previous anti-fungal agents is needed.

Although medicine has advanced, plants still play a key role for health care. See Ponnusamy, K., Petchiammal, C., Mohankumar, R., & Hopper, W. (2010), "In vitro antifungal activity of indirubin isolated from a South Indian ethnomedicinal plant" Wrightia tinctoria, 349-354, incorporated herein by reference in its entirety. In most cases, natural medicines are more effective and preferred over synthetic ones. Abulyazid in 2010 mentioned that naphthoquinones show great pharmacological properties as they are cytotoxic, with antibacterial, antifungal, antiviral, insecticidal, anti-inflammatory, and antipyretic properties. See Abulyazid, I., Mahdy, E. M. E., Ahmed, R. M., 2010. "Biochemical study for the effect of henna (*Lawsonia inermis*) on *Escherichia coli*" Arabian Journal of Chemistry and Babu, P. D. and Subhasree, R. S. 2009. "Antimicrobial Activities of *Lawsonia inermis*—A Review" Academic Journal of Plant Sciences, 2, 231-232, each incorporated herein by reference in their entirety. A phytopharmacological review by Chaudhary as mentioned above in 2010 reported that this henna has analgesic, hypoglycemic, hepatoprotective, immunostimulant, anti-inflammatory, antibacterial, antimicrobial, antifungal, antiviral, antiparasitic, antitrypanosomal, antidermatophytic, antioxidant, antifertility, tuberculostatic and anticancer properties. See Chaudhary, G., Goyal, S., & Poonia, P. (2010), "*Lawsonia inermis* Linnaeus: a phytopharmacological review" International Journal of Pharmaceutical Sciences and Drug Research, 2(2), 91-98, incorporated herein by reference in its entirety.

Henna was implicated to have other pharmacological uses as an antitumor agent, anthelmintic, antioxidant, immunomodulatory, burn wound healing, UV protective and antimicrobial properties. See Bairagi, G.; Kabra, A., Mandade, R. "Anthelmintic activity of *Lawsonia inermis* L. leaves in Indian adult earthworm," Int, J. Res. Pharm. Biomed. Sci. 2011, 2, 237-240, Mikhaeil, B. R., Badria, F. A., Maatooq, G. T., Amer, M. "Antioxidant and immunomodulatory constituents of henna leaves," Z. Naturforschung C 2004, 59, 468-476. Muhammad, H., Muhammad, S. "The use of *Lawsonia inermis* Linn. (Henna) in the management of burn wound infections," Afr. J. Biotechnol. 2005, 4, 934-937, Dweck, A. C. "Natural ingredients for colouring and styling," Int. J. Cosmet. Sci. 2002, 24, 287-302, Saadabi, M. A. A. "Evaluation of *Lawsonia inermis* Linn. (Sudanese Henna) leaf extracts as an antimicrobial agent," Res. J. Biol. Sci. 2007, 2, 419-423, incorporated herein in its entirety.

Due to the wide application of henna in hair coloration and body paints, numerous studies have been conducted to determine any potential health hazards of henna. Chaudhary et al, found in their review article in 2010 that henna can have hypoglycaemic and hypolipidaemic activities in alloxan induced diabetic mice after oral administration. In 2008 it was announced that the feeding of 0.8 g/kg of *L. inermis* extract decreased the concentration of glucose, cholesterol and triglycerides to normal.

A review done by Kluger in 2008 mentioned that the allergies develop when a particularly powerful allergen is added to henna in order to decrease the time of developing the color upon applying henna to the skin. The commonly used additive which causes the allergic reaction is para-phenylenediamine (PPD). See Kluger, N., Raison-Peyron, N., & Guillot, B. (2007), "Temporary henna tattoos: Sometimes serious side effects" Presse medicale (Paris, France: 1983), 37(7-8), 1138-1142, incorporated herein by reference in its entirety. Another study declared that the cause of allergy is due to many chemical coloring agents, such as diaminotoluenes and diaminobenzenes or additives mainly oils or paraphenylenediamine which could cause contact dermatitis and this means adverse health potential on human. See Brancaccio, R. R., Brown, L. H., Chang, Y. T., Fogelman, J. P., Mafong, E. A., & Cohen, D. E. (2002), "Identification and quantification of para-phenylenediamine in a temporary black henna tattoo" Dermatitis, 13(1), 15-18; and Al-Suwaidi, A., & Ahmed, H. (2010), "Determination of para-phenylenediamine (PPD) in henna in the United Arab Emirates" International journal of environmental research and public health, 7(4), 1681-1693, each incorporated herein by reference in their entirety.

Studies indicated that methylation of lawsone leads to lawsone methyl ether, which is used as a mouthwash and possesses potent antifungal activity both in vitro and in vivo studies. See Panichayupakaranant, P. and Reanmongkol, W. 2002, "Evaluation of Chemical Stability and Skin Irritation of Lawsone Methyl Ether in Oral Base" Pharmaceutical Biology, 40, 429-432, incorporated herein by reference in its entirety. Fransworth and Cordell reviewed the value of minimal fungicidal concentration of Lawsone methyl ether (2-methoxy-1,4-napthoquinone) (LME) against Candida as 1.25 1 g/ml. See Sritrairat, N., Nukul, N., Inthasame, P., Sansuk, A., Prasirt, J., Leewatthanakorn, T., & Chanowanna, N. (2011), "Antifungal activity of lawsone methyl ether in comparison with chlorhexidine" Journal of oral pathology & medicine, 40(1), 90-96, incorporated herein by reference in its entirety.

Kirkland and Marzin in 2003 and 2004 declared that henna has no genotoxic risk to the consumers. See Kirkland, D., & Marzin, D. (2003), "An assessment of the genotoxicity of 2-hydroxy-1, 4-naphthoquinone, the natural dye ingredient of Henna" Mutation Research/Genetic Toxicology and Environmental Mutagenesis, 537(2), 183-199; Marzin, D., & Kirkland, D. (2004); "2-Hydroxy-1, 4-naphthoquinone, the natural dye of henna, is non-genotoxic in the mouse bone marrow micronucleus test and does not produce oxidative DNA damage in Chinese hamster ovary cells" Mutation Research/Genetic Toxicology and Environmental Mutagenesis, 560(1), 41-47, each incorporated herein by reference in their entirety. Selvanayaki and T. Ananthiin (2012) have recently studied the hepatoprotective activity of aqueous extract of lawsonia inermis against paracetamol induced rats by administering the aqueous extract of lawsonia inermis orally to the rats with hepatotoxicity induced by paracetamol and concluded that the aqueous extract of lawsonia inermis possesses hepatoprotective activity against paracetamol induced hepatotoxicity in rats. See Selvanayaki, R., & Ananthi, T. 2012, "Hepatoprotective Activity of Aqueous Extract of Lawsonia inermis against Paracetamol Induced Rats," Asian J. Pharm. Res., 2, 75-77, incorporated herein by reference in its entirety. Another study in 2005 measured the toxicity against human cancer cells of plants used in traditional medicine in Yemen, henna was one of studied plants (named hana or Lawsonia inermis L.) and it was effective. See Al-Fatimi, M., Friedrich, U., Jenett-Siems, K. 2005, "Cytotoxicity of plants used in traditional medicine in Yemen," Fitoterapia, 76, 355-358, incorporated herein by reference in its entirety.

Henna leaves have anti-Candida Albicans effect. See Abdulyazid, I., Mahdyl, E. M. E., Ahmed, R. M. 2010, "Biochemical study for the effect of henna (Lawsonia inermis) on Escherichia coli" Arabian Journal of Chemistry, incorporated herein by reference in its entirety. Tripathi et al. (1977) found that the leaves of Lawsonia inermis exhibited a strong fungi toxicity effect due to the presence of 2-hydroxy-1,4-naphthoquinone (Lawsone). See Tripathi, R. D., Srivastava, H. S., Dixit, S. N. 1978, "A fungitoxic principle from the leaves of Lawsonia inermis," Lam Experientia, 34, 51-52, incorporated herein by reference in its entirety.

In view of the forgoing, one objective of the present disclosure is to provide a denture and a denture coating composition that includes henna and natural products in henna to e the growth, pathogenic effect of Candida albicans, and associated denture stomatitis.

BRIEF SUMMARY OF THE INVENTION

According to a first aspect, the disclosure describes a denture having a first antimicrobial ingredient, wherein the first antimicrobial ingredient is a henna powder or a henna extract, each of which comes from pulverized henna leaves and comprises at least one compound selected from the group consisting of lawsone, tannic acid, and 2-methoxy-1, 4-napthoquinone, a second antimicrobial ingredient, and a denture fabrication material. The first antimicrobial ingredient coats the surface of the denture fabrication material and extends into the interior of the denture fabrication material.

In some embodiments of the denture, the denture fabrication material comprises a cured acrylic resin which is poly(methyl methacrylate).

In some embodiments of the denture, a cured acrylic resin which is poly(ethyl methacrylate), poly(butyl methacrylate), or mixtures thereof.

In some embodiments of the denture, the denture comprises 0.1% to 20% w/w of a total weight of the first antimicrobial ingredient relative to a total weight of the denture.

In some embodiments of the denture, the denture further includes a biocompatible gel which is a hydrogel or a polymer gel.

In some embodiments of the denture, the denture further includes an odor neutralizer, which is two or more aldehydes selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, bucinal, thiophene carboxaldehyde, trans-4-decenal, trans trans 2,4-nonadienal, and undecyl aldehyde.

According to a second aspect, the disclosure describes a denture having a first antimicrobial ingredient, wherein the first antimicrobial ingredient is a henna powder or a henna extract, each of which comes from pulverized henna leaves and comprises at least one compound selected from the group consisting of lawsone, tannic acid, and 2-methoxy-1, 4-napthoquinone, a second antimicrobial ingredient, and a denture fabrication material. The first antimicrobial ingredient, the second antimicrobial ingredient, or both coat the surface of the denture fabrication material and extend into the interior of the denture fabrication material.

In some embodiments of the denture, the second antimicrobial ingredient is a silver nanoparticle, a titanium dioxide particle, a silicon compound or an essential oil.

In some embodiments of the denture, the second antimicrobial ingredient is the silver nanoparticle, and the silver nanoparticle has an average diameter of 40 nm to 80 nm.

In some embodiments of the denture, the second antimicrobial ingredient is the titanium dioxide particle, and the titanium dioxide particle has an average diameter of 40 nm to 160 nm.

In some embodiments of the denture, the second antimicrobial ingredient is the essential oil, and the essential oil is at least one selected from the group consisting of lemongrass oil, peppermint oil, neem oil, orange oil, palmarosa oil, and patchouli oil.

In some embodiments of the denture, the denture comprises 0.1% to 25% w/w of a total weight of the first antimicrobial ingredient and the second antimicrobial ingredient relative to a total weight of the denture.

In some embodiments of the denture, the denture further includes a third antimicrobial ingredient comprising 3-alkyl-2-hydroxy-1,4-napthoquinone, 2-amino-1,4-napthoquinone, and/or 3-aminophenyl-2-hydroxy-1,4-napthoquinone.

In some embodiments of the denture, the denture comprises 0.1%-5% w/w of third antimicrobial ingredient relative to a total weight of the denture.

In some embodiments of the denture, the denture further includes a biocompatible gel which is a hydrogel or a polymer gel.

In some embodiments of the denture, the denture further includes an odor neutralizer, which is two or more aldehydes selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, bucinal, thiophene carboxaldehyde, trans-4-decenal, trans trans 2,4-nonadienal, and undecyl aldehyde.

In some embodiments of the denture, the denture fabrication material comprises a cured acrylic resin which is poly(methyl methacrylate).

In some embodiments of the denture, a cured acrylic resin which is poly(ethyl methacrylate), poly(butyl methacrylate), or mixtures thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Throughout the specification ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

An aspect of the present disclosure describes a denture having a first antimicrobial ingredient, wherein the antimicrobial ingredient is a henna powder or a henna extract, a denture fabrication material, and optionally, a second antimicrobial ingredient. The henna powder and henna extract may have at least one compound selected from the group consisting of lawsone, tannic acid, and 2-methoxy-1,4-napthoquinone. The first antimicrobial ingredient and, optionally, the second antimicrobial ingredient, may coat the surface of the denture fabrication material and extend into the interior of the denture fabrication material. In some embodiments, the first antimicrobial ingredient and the optional second antimicrobial ingredient may be integrated into the denture fabrication material.

A study exploring the present disclosure included a control group wherein no henna powder, extract, or combination thereof was added to compare with other specimens where henna was incorporated with the denture acrylic resin.

Figure 1:
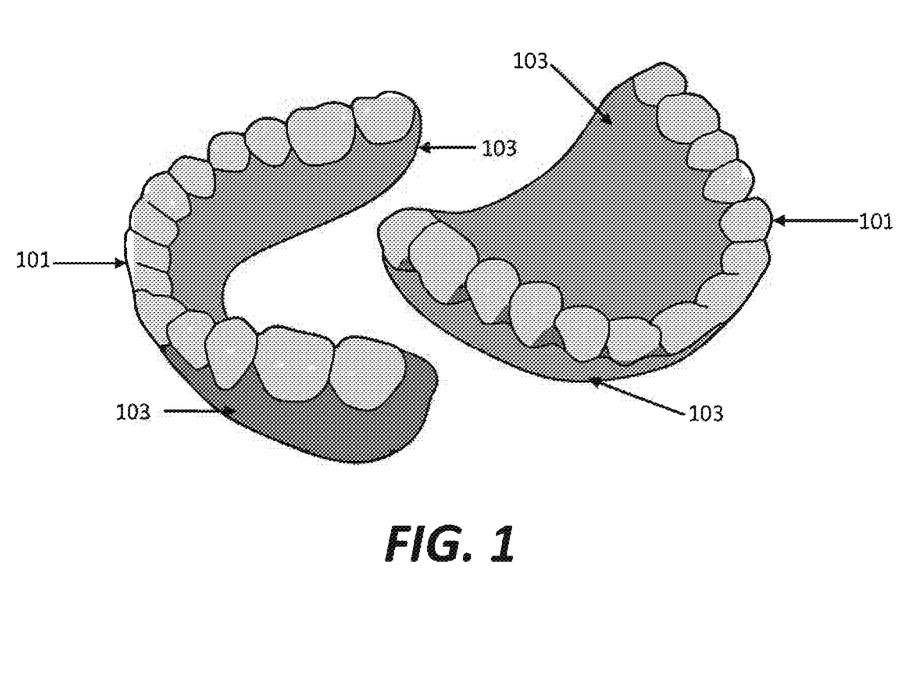
FIG. 1 is an exemplary depiction of a denture of the present disclosure.

Commonly dentures are custom prepared to fit in a patient's mouth. The denture, as depicted in FIG. 1, comprises two main parts: the teeth 101 and the gums 103. The gums 103 may be considered a soft-tissue part of the denture or a denture base, whereas teeth 101 may be considered a non-soft-tissue part of the denture. The soft-tissue part of the denture covers and contacts the soft oral mucosa and creates a base for the non-soft tissue part of the denture, the teeth 101. The first antimicrobial ingredient as described herein, may contact the soft-tissue part of the denture and may include various colors to mimic a natural color of the gums and oral mucosa. Further, the henna extract may contact the non-soft tissue part of the denture. Denture fabrication materials may be curable polymers and plastics commonly prepared from acrylic resin, nylon, or both. Further, commercial products such as Valplast®, Flexite®, DuraFlex®, and TCS® may be included in the denture fabrication material of the present disclosure. The commercial products mentioned above, the acrylic resin, the nylon and combinations thereof may be combined to produce a denture as described by the present disclosure. The weight percent of denture fabrication material relative to a total weight of the denture may be about 50%-95%, about 55%-90%, about 60%-85%, about 65%-80%, or about 70% to 75%.

The acrylic resin describes a variety of resins including but not limited to reacted forms of methyl methacrylate, ethyl methacrylate, butyl methacrylate, n-butyl methacrylate, i-butylmethacrylate, hexylmethacrylate, dicyclopentenylmethacrylate, tetrahydrofurfurylmethacrylate, 2-hydroxyethylmethacrylate, glycidylmethacrylate, laurylmethacrylate, cyclohexylmethacrylate, benzylmethacrylate, allylmethacrylate, 2-ethoxyethyl methacrylate, methoxy polyethylene glycolmethacrylate, glycerol methacrylate, and isobornyl methacrylate. The resin may further include nitrogen-containing compounds in reacted form, such as 2-(N,N-dimethylamino)ethylmethacrylate, N-methylolmethacrylamide and diacetonemethacrylamide. The resin may further include silane compounds in reacted form such as gamma-methacryloyloxypropyl trimethoxysilane and gamma-methacryloyloxypropyl triethoxysilane.

The acrylic resin may include multi-functional resins in reacted form including, but not limited to 2-hydroxy-3-acryloyloxypropyl methacrylate, hydroxypivalic acid neopentyl glycol dimethacrylate, ethylene glycol dimethacrylate, diethylene glycol dimethacrylate, triethylene glycol dimethacrylate, butylene glycol dimethacrylate, pentaerythritol tetra(meth)acrylate and ditrimethylolpropane tetra(meth)acrylate.

The present disclosure describes the use of henna powder and/or henna extract in the denture. Henna or as named *Lawsonia inermis*, is considered as folklore medicines in Tamil Nadu and India. It is extensively used in the treatment of ringworm infections and skin related diseases that are considered as one of the major threats in the field of medicine. Henna is a plant that is targeted for anti-fungal properties. Henna is a traditionally used plant with religious associations. See Zohourian, T. H., Quitain, A. T., Sasaki, M., & Goto, M. (2011), "Polyphenolic contents and antioxidant activities of *Lawsonia inermis* leaf extracts obtained by microwave-assisted hydrothermal method" Journal of Microwave Power and Electromagnetic Energy, 45(4), 193-204, incorporated herein by reference in its entirety. Henna may be characterized by its natural reddish pigment obtained from the dried leaves of a plant *L. inermis*. When henna is mixed with water it forms a paste that can be applied directly to the skin. Darker skin tones can be obtained with longer durations of contact. See Ramírez-Andreo, A, Hernández-Gil, A., Brufau, C., Marín, N., Jiménez, N., Hernández-Gil, J., & Soria, C. (2007) "Allergic contact dermatitis to temporary henna tattoos." Actas Dermo-Sifiliográficas (English Edition), 98(2), 91-95, incorporated herein by reference in its entirety.

Van Braak noted that henna (*Lawsonia inermis*) is part of the family *Lythraceae*, used as a natural dye. See Van Braak, H. (2001) "Natürliches Henna" Niedernhausen: Falken Verlag, 10-7, incorporated herein by reference in its entirety. Carl Linnaeus, the famous Swedish botanist, gave it the name of his assistant, the Scottish physician, Isaac Lawson. Inermis is Latin for "unarmed;" when henna is cultivated, it loses its thorns. See Kazandjieva, J., Grozdev, I., & Tsankov, N. (2007) "Temporary henna tattoos" *Clinics in dermatology*, 25(4), 383-387, incorporated herein by reference in its entirety. It is a small tree, planted mainly for its leaves. This plant is commonly known as henna or mhendi and abundantly available in tropical and subtropical areas. It is well known and used all over the world. See Chaudhary, G., Goyal, S., & Poonia, P. (2010), "*Lawsonia inermis* Linnaeus: a phytopharmacological review" International Journal of Pharmaceutical Sciences and Drug Research, 2(2), 91-98; and Bele, A. A., Jadhav, V. M., & Kadam, V. J. (2010) "Potential of tannnins: a review" Asian Journal of Plant Sciences, 9(4), 209, each incorporated herein by reference in their entirety. Historically, henna was used to temporarily color skin and hair by applying it to the skin for several hours for compounds from henna to be absorbed, which results in brownish orange stain. See Yusuf, M., Ahmad, A., Shahid, M., Khan, M. I., Khan, S. A., Manzoor, N., & Mohammad, F. (2012), "Assessment of colorimetric, antibacterial and antifungal properties of woolen yarn dyed with the extract of the leaves of henna (*Lawsonia inermis*)" Journal of Cleaner Production, 27, 42-50, incorporated herein by reference in its entirety.

Henna is composed of natural tannin named hennotannic acid or lawsone. This tannin has the ability of tannins to inhibit the growth of many fungi, yeasts, bacteria and viruses. Dried powdered leaves of henna also contains about 0.5 to 1.5% lawsone, the main component for dyeing properties of henna lawsone, the dye molecule in henna will bind with protein, such as the keratin in fingernails, hair and skin. Other components of henna are mannite, tannic acid, 2-hydroxy-1,4-naphthoquinone resin mucilage, gallic acid, glucose, mannitol, and fat. The coloring matter includes quinone and napthaquinone.

Henna is a natural product, which is safely used without adverse side effects. Any side effects of the usage of commercial henna are mainly allergic reactions resulting from additives.

The henna, as used herein, may be a henna powder, which may be produced from pulverized dried henna leaf, dried henna root, henna flowers, or dried henna stems. Most preferably the henna powder is produced from dried young henna leaf. The henna powder may have particles of a size of less than about 150 µm, less than about 100 µm, less than about 75 µm, less than about 60 µm, less than about 50 µm, less than about 40 µm, less than about 30 µm, or less than about 25 µm, but no less than about 5 µm.

Henna extract may be obtained from henna powder, henna leaf, pulverized henna leaf, henna root, henna flower, or henna seeds. The henna may be extracted by methods including but not limited to distillation, steam distillation, pressing, organic extraction, or additional extraction methods known to those familiar in the art. The henna extract, the henna powder, or both may be combined with the denture fabrication material prior to curing by mechanical mixing, blending, and stirring with mechanical the implements in a mixing vessel. The mixing may continue for 1-10 minutes, for 2-8 minutes, 3-7 minutes, or for 4-6 minutes until the henna extract is evenly distributed with the denture fabrication material in the mixing vessel. A weight percent of henna extract and/or henna powder relative to a total weight of the denture may be about 0.1%-20%, about 1%-18%, about 2%-15%, about 4%-10%, or preferably about 6%-8%.

The henna powder and the henna extract may include lawsone, tannic acid, or 2-methoxy-1,4-napthoquinone. The henna powder and the henna extract may each include lawsone, tannic acid, and/or 2-methoxy-1,4-napthoquinone in a percentage by weight relative to the total weight of the henna powder or the henna extract of about 0.1%-95%, about 1%-90%, about 2%-80%, about 4%-70%, about 6%-60%, about 8%-50%, about 10%-40%, about 15%-30%, or about 20%-25%. In some embodiments, the henna powder and/or the henna extract may further include mannite, mucilage, and/or gallic acid in a percentage by weight relative to the total weight of the henna powder or the henna extract of about 0.05%-10%, about 0.1%-9%, about 1%-8%, about 2%-7%, about 3%-6%, or about 4%-5%.

2-methoxy-1,4-naphthoquinone

In some embodiments the antimicrobial ingredients described herein may be effective in treating bacteria and fungus including, but not limited to gram positive and gram negative bacteria, candidal, and non-candidal fungi. Gram positive bacteria may include, but is not limited to pathogens such as *Staphylococcus aureus, Streptococcus pyogenes* and *Clostridium botulinum*. Gram negative bacteria may include, but is not limited to pathogens such as *Salmonella, Escherichia coli, Klebsiella, Haeophilus, Pseudomonas aeruginosa, Proteus* and *Shigella dysenteriae*. Gram negative bacteria are generally distinguished from Gram positive by an additional protective cell membrane. Non-candidal oral mycoses that may be susceptible to the antimicrobial ingredients described herein may include, but are not limited to *aspergillus, cryptococcus, histoplasma, blastomyces, paracoccidioides*, and *zygomycota*.

In some embodiments, the second antimicrobial ingredient is a silver nanoparticle, a titanium dioxide particle, a silicon compound or an essential oil. The silver nanoparticles, the titanium dioxide particles, the silicon compound or the essential oil may provide broad spectrum protection from pathogenic bacterial or fungal infection inside a patient's mouth as well as aid in the cleaning process of dentures outside the mouth.

The antimicrobial properties of silver nanoparticles stem from the chemical properties of silver's ionized form, $Ag^+$, and several mechanisms have been proposed to explain this effect. For example, silver ions form strong molecular bonds with other substances used by bacteria to respire, such as enzymes containing sulfur, nitrogen, and oxygen. When the $Ag^+$ ion forms a complex with these biomolecules, they are rendered inactive, depriving them of necessary activity and eventually leading to the bacteria's death. Silver ions can also complex with bacterial DNA, impairing the ability of the microorganisms to reproduce. In some embodiments of the denture in which the second antimicrobial ingredient is the silver nanoparticle, the silver nanoparticle has an average diameter of about 40 nm to 80 nm, about 45 nm to 75 nm, about 50 nm to 70 nm, or about 55 nm to 65 nm.

Titanium dioxide nanoparticles have a broad spectrum of activity against microorganisms, including Gram-negative and positive-bacteria and fungi, which may be of particular importance for multiple drug resistant strains. Further, the titanium dioxide nanoparticles exert a non-contact biocidal action. Therefore, no release of potentially toxic nanoparticles to the saliva is required to achieve disinfection capabilities. In some embodiments of the denture in which the second antimicrobial ingredient is the titanium dioxide particle, the titanium dioxide particle has an average diameter of about 40 nm to 160 nm, about 50 nm to 150 nm, about 60 nm to 140 nm, about 70 nm to 130 nm, about 80 nm to 120 nm, or about 90 nm to 110 nm.

Silicon compounds which may include silicon dioxide nanoparticles have been found to inhibit bacteria adherence to oral biofilms. A biofilm is any group of microorganisms in which cells stick to each other and often these cells adhere to a surface, such as a solidified dental fabrication material or denture as described herein. These adherent cells are frequently embedded within a self-produced matrix of extracellular polymeric substance (EPS). Biofilm extracellular polymeric substance is a polymeric conglomeration generally composed of extracellular DNA, proteins, and polysaccharides. Biofilms may form on living or non-living surfaces and can be prevalent in natural, industrial and hospital settings. Although not strictly having a toxic mechanism, the silicon compounds and nanoparticles may induce an unfavorable change in the biofilm to reduce the adhesion, and therefore proliferation of bacteria and fungus. The silicon compound may include, but is not limited to 3-(trimethoxysilyl)propyldimethyloctadecyl ammonium chloride, 3-(trimethoxysilyl)propylmethyldi(decyl) ammonium chloride, 3-chloropropyltrimethylsilane, octadecyltrimethoxysilane, perfluorooctyltriethoxysilane, ethyltrimethoxysilane, vinyltrimethoxysilane, or vinyltriacetoxysilane. Silicon dioxide nanoparticles may be an average spherical size of about 10-30 nm, about 12-28 nm, about 15-25 nm, or about 18-23 nm.

Essential oils have been shown to possess antibacterial, antifungal, antiviral insecticidal, and antioxidant properties. Some oils have been used in cancer treatment, food preservation, aromatherapy, and fragrance industries. Essential oils are a rich source of biologically active compounds. Essential oils are aromatic oily liquids obtained from plant materials (flowers, buds, seeds, leaves, twigs, bark, herbs, wood, fruits and roots). They can be obtained by expression, fermentation or extraction but the method of steam distillation is most commonly used for commercial production. In some embodiments of the denture, the second antimicrobial ingredient is the essential oil, and the essential oil may include but is not limited to lemongrass oil, peppermint oil, neem oil, orange oil, palmarosa oil, and patchouli oil. In some embodiments, the essential oil may be a complex mixture of different organic molecules—terpenes, alcohols, esters, aldehydes, ketones and phenols.

In some embodiments of the denture, a total weight of the first antimicrobial ingredient and, optionally, the second antimicrobial ingredient relative to a total weight of the denture may be about 0.1% to 25%, about 0.5% to 22%, about 1% to 20%, about 2% to 18%, about 5% to 15%, about 8% to 13%, about 10% to 11%. In some embodiments of the denture coating composition, the denture coating composition comprises a weight percent of the first antimicrobial ingredient relative to a total weight of the denture coating composition 0.1% to 20%, about 0.5% to 18%, about 1% to 15%, about 5% to 13%, about 10% to 11%.

In some embodiments of the denture, the denture further includes a third antimicrobial ingredient including, but not limited to 3-alkyl-2-hydroxy-1,4-napthoquinone, 2-amino-1,4-napthoquinone, and/or 3-aminophenyl-2-hydroxy-1,4-napthoquinone. The term alkyl can refer to two or more carbons linked, which may be branched, linear, or cyclic. The third antimicrobial ingredient may be a derivative of lawsone. The derivative may further include an amine derivative of lawsone, a halogenated derivative of lawsone, an alkoxy derivative of lawsone, and a halogen-substituted phenyl derivative of lawsone. For example, the derivative may be 3-amino-2-chloro-1,4-naphthoquinone, 5,8-Dimethoxy-1,4-naphthoquinone, or 3-iodo-2-hydroxy-naphthoquinone. In some embodiments of the denture, the denture comprises a concentration of third antimicrobial ingredient relative to the denture by weight of about 0.1%-5%, about 0.5% to 4.5%, about 1% to 4%, about 2% to 3.5%, or about 2.5% to 3%.

In some embodiments of the denture, the denture may be prepared by combining the first, second, and/or the third antimicrobial ingredients into the dental fabrication material, prior to curing, by mechanical mixing, blending, and stirring with mechanical implements in a mixing vessel. The mixing may continue for 1-10 minutes, for 2-8 minutes, 3-7 minutes, or for 4-6 minutes until the first, second, and/or third antimicrobial ingredient is evenly distributed with the denture fabrication material in the mixing vessel. The denture fabrication material, once mixed, may be injected into a mold configured to resemble a patient's mouth. The injected denture fabrication material may be cured in the mold to form a cured denture base or a part of the cured denture base, in some embodiments the denture fabrication material mixed with the first antimicrobial ingredient, the second antimicrobial ingredient, and/or the third antimicrobial ingredient may be a surface coating layer of the denture base. Heat-activated curing, cold curing, and/or light-based curing methods may be employed for the denture material of the present disclosure. Heat-activated curing may include applying heat to the mold via a hot-water bath, heating element, or heat lamps causing the polymerization f the denture fabrication material inside the mold. A light-based curing may be a curing process in which light may be used to create a photochemical reaction that cures polymers such as those comprising the denture fabrication material as described herein. Cold curing is auto-polymerization of the denture fabrication material caused by a chemical reaction rather than a result of applying heat or light once cured, the denture base may be removed from the mold to be prepared for false teeth.

In some embodiments of the denture, the first antimicrobial ingredient, the second antimicrobial ingredient, or both coat the surface of the denture fabrication material and extend into the interior of the denture fabrication material and are cured to form the denture. In some embodiments of the denture, the first, second, and/or third antimicrobial ingredients coat the surface of the denture fabrication material and extend into the interior of the denture fabrication material and are cured to form the denture. The phrase "extend into the interior" implies a gradient in which the antimicrobial ingredient or antimicrobial ingredients on the surface of the denture are at higher concentration that the antimicrobial ingredient or antimicrobial ingredients in the interior of the denture. In some embodiments, the first, the second, and/or the third antimicrobial ingredient may be uniformly dispersed throughout the entire denture.

In some embodiments of the denture, the denture further includes a biocompatible gel which is a hydrogel or a polymer gel. The biocompatible gel may be a coaxing for the denture or may be integrated into the denture fabrication material. When the biocompatible gel is a coating, the biocompatible gel is a second layer on the denture after the denture fabrication material. For example, the denture may be coated with the denture fabrication material in combination with the antimicrobial ingredients, then the biocompatible gel may be coated over the denture fabrication material, or the biocompatible gel may be combined with the antimicrobial ingredients in addition to the denture fabrication material. The weight percent of biocompatible gel refers to a total denture weight that has an amount of the biocompatible gel that is about 0.1%-5%, about 0.5% to 4.5%, about 1% to 4%, about 2% to 3.5%, or about 2.5% to 3%. Hydrogel and/or polymer gels may include natural polymers such as glycosaminoglycans, polysaccharides, proteins, and the like, as well as synthetic polymers, as are generally known in the art. A non-limiting list of polymeric materials that can be utilized in forming the hydrogel can include collagen, dextran, hyaluronic acid, chitin, heparin, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

Hydrogel or a polymer gel may be formed according to any method as is generally known in the art. For instance, a hydrogel can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, a hydrogel can be polymerized in the presence of an initiator. For example, in one embodiment, a hydrogel mesh can be photopolymerized in the presence of a suitable initiator such as Irgacuree or Darocur® photoinitiators available from Ciba Specialty Chemicals.

Denture stomatitis may also result in malodor in the mouth of a patient. In some embodiments of the denture, the denture further includes an odor neutralizer, which is two or more aldehydes selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, bucinal, thiophene carboxaldehyde, trans-4-decenal, trans trans 2,4-nonadienal, and undecyl aldehyde The odor neutralizer may be mixed into the denture fabrication material or the biocompatible gel to be included in the denture. A weight percentage of the odor neutralizer in the denture may be 0.001%-5%, about 0.01% to 4.5%, about 0.1% to 4%, about 1% to 3.5%, about 1.5% to 3%, or about 2.0% to 2.5%.

According to a second aspect, the present disclosure describes a denture having at least one first antimicrobial ingredient selected from the group consisting of henna powder, henna extract, lawsone, tannic acid, and 2-methoxy-1,4-napthoquinone, and a second antimicrobial ingredient, and optionally, a biocompatible gel and an odor neutralizer. The first antimicrobial ingredient and the second antimicrobial ingredient included in the denture are as described above. Further, the biocompatible gel and the odor neutralizer are as described above.

The denture may be prepared by mixing the biocompatible gel with the first and the second antimicrobial ingredient and the odor neutralizer with the denture fabrication material. Further, the third antimicrobial ingredient, as described herein may be included in the mixture of the denture. The mixing may be accomplished by mechanical mixing as described herein.

In some embodiments, the denture may further include flavoring. The flavoring may include, but is not limited to cinnamon, peppermint, vanilla, bubble gum, honey, fruit flavors, and or a sweetener or synthetic sweetener. Flavoring may include natural flavors, synthetic flavors, or combinations thereof. A weight percentage of the flavoring in the denture may be 0.001%-5%, about 0.01% to 4.5%, about 0.1% to 4%, about 1% to 3.5%, about 1.5% to 3%, or about 2.0% to 2.5%.

In some embodiments, the denture may further include a water-soluble fluoride compound in an amount sufficient to give a fluoride ion concentration in the composition, and/or when it is used of from about 0.0025% to about 5.0% by weight or from about 0.005% to about 2.0% by weight. A wide variety of fluoride ion-yielding materials can be employed as sources of soluble fluoride in the present compositions. Exemplary fluoride ion sources include, but are not limited to stannous fluoride, sodium fluoride, potassium fluoride, sodium monofluorophosphate, indium fluoride, ammonium fluoride and many others. Stannous fluoride and sodium fluoride are among preferred sources, as well as mixtures thereof.

The examples below are intended to further illustrate the effectiveness of henna powder activity against *C. albicans* growth and are not intended to limit the scope of the claims.

EXAMPLE

The experimental details described herein may be found in a publication by the inventors. See Nawasrah, Amal, AlNimr, Amani, and Ali, Aiman A. "Antifungal Effect of henna against *Candida albicans* Adhered to Acrylic Resin as a Possible Method for Prevention of Denture Stomatitis," Int. J. Environ, Res. Public Health 2016, 13(5), 520, incorporated herein by reference in its entirety.

Sample Size and Specimen Preparation

One hundred eighty acrylic plates were prepared of heat cured acrylic (Trevalon/Universal Clear—DENTSPLY. Germany) with powder and liquid ratio similar to the one made for complete denture. The specimens were divided into 6 groups of 30 samples each. The first group was only polymer and monomer following the conventional manufacturer instruction for processing complete denture. The other five groups were processed by adding different concentration of Yamani henna powder (Harazi) to the polymer in a concentration of henna: polymer of 1%, 2.5%, 5%, 7.5% and 10% respectively. Samples were fabricated at the prosthodontic laboratory in the College of Dentistry, University of Dammam, with dimension of 20×10×3 mm. Samples were incubated in artificial saliva rich with *Candida albicans* at 37° C., and the effect of Henna on *Candida albicans* was evaluated in 2 different methods: semi-quantitative slide count and a culture-based quantitative assay (quantitative).

Exposing Acrylic Specimens to *Candida Albicans*

All acrylic plates were immersed in artificial saliva that contains 2,000,000 cells of *Candida albicans* (ATCC 10231) and incubated in 37° C. for 2 weeks. All the samples were then washed with tap water and subjected for evaluation of the number of *Candida albicans* attached and proliferated on the surface of acrylic resin samples.

Evaluation

Two methods of evaluation were used to calculate the number of living *Candida albicans* adhered to each acrylic resin sample as follows. After washing each plate with tap water, the plates were incubated in a broth agar at 37° C. for 48 hours then vibrated using vertex followed by centrifuging the tubes with specimens to get the concentrated billet of *C. albicans*. Then the following two methods of evaluation were used for each specimen.

(1) Slide count: 2.5 µl of Trypan Blue 0.4% solution in Phosphate (MP-Biomedicals) was added to 7.5 µl of each sample to be placed on a slide count (Nebauer Slide Counter "Chambers-Marienfeld") for microscopic evaluation. With Trypan Blue stain, dead *C. albicans* would appear blue in color while live *Candida* would appear transparent with blue border line. Therefore, with Trypan Blue stain, it was possible to count the number of living *C. albicans*. Trypan Blue stain should allow counting the number of *Candida* under light microscope at 10×10 magnifications. Slide count usually contains 4 main squares; each is divided into 16 squares. *C. albicans* was counted in 2 main squares and multiplied by 2 to get the total number of cells in the slide.

(2) Direct culture test: 10 µl of each sample was taken and spread on a petri dish and then it was incubated at 37° C. for 48 hours. Colonies of *C. albicans* were counted in the samples using marker pen counter (colony counter "Scienceware Bel-Art Products"). If the number of colonies that cover the whole surface of the petri dish was more than 500 it was considered as overgrowth.

Statistics

Figure 2:
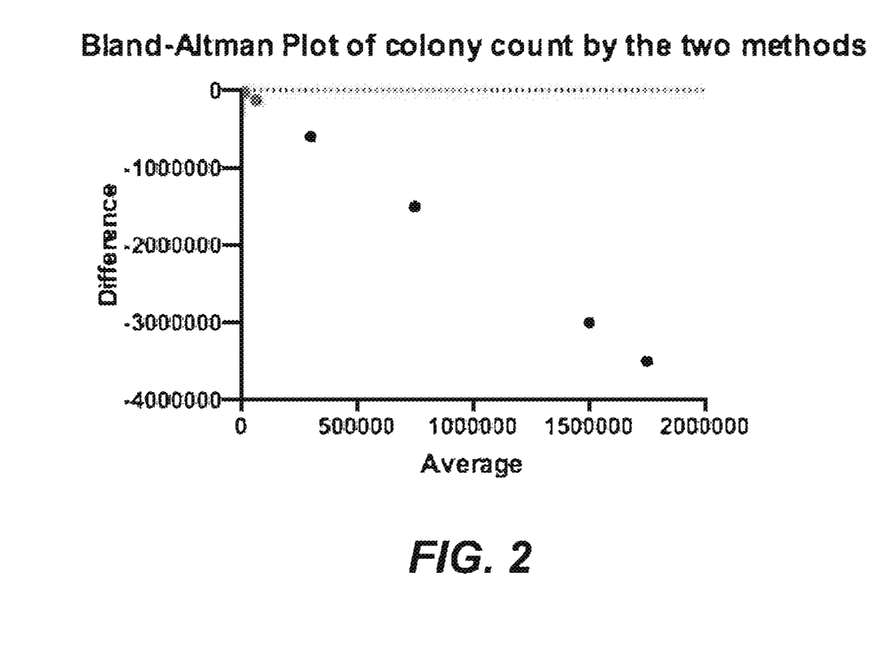
FIG. 2 is a Bland-Altman plot of colony counts comparing slide count and direct culture test methods.

Because the discrete colony count values varied widely, the mode method was used to represent the results. Log reduction of each concentration by both methods was reported with p-value calculated by the paired t-test to check for robustness. To compare the performance of the two assays, Bland-Altman plot was performed (Bland and Altman, 1986) using Graph Pad 6.0 to illustrate method agreement as shown in FIG. 2. The Bland-Altman diagram plotted the difference in average counts between the two methods. All results for all concentration and growth control were included in the analysis. The software calculated the bias which represents the average discrepancy between the methods, and the upper and lower levels of agreement (LOA) calculated as bias +/−1.96× standard deviation of the bias. The closer the bias to zero and the narrower limits of agreement indicate that the methods are in agreement.

Results

Slide Count

Referring to Table 1, live *C. albicans* colonies were counted for the group A (Control) to group F by using slide count method. Variation in the number of living *C. albicans* cells was observed with the increase in the concentration of Yamani henna powder (Harazi). It was observed that the variation in live *C. albicans* colonies between control group (i.e. group A) and group B (concentration of Yamani henna powder was 1%), was statistically significant with p-value of 0.0001. Similarly, variations in live *C. albicans* colonies were significant, when the concentration of powder was 7.5% or 10% in contrast with control group A and p-values were 0.0001 and 0.001 respectively.

Direct Culture Test

The number of living *C. albicans* cells was checked by culture test and mean and standard deviation was determined for each test group (A-F). Variation of live *C. albicans* for each experimental group, B-F, in comparison with control group, A, was checked for statistical significance. Test for analysis of variance (ANOVA) was employed and found that when the concentrations of henna powder was 1%, 10% the results were significant with p-values 0.001 and 0.01 respectively.

Statistical difference, in the mean number of live *C. albicans* by using two different methods, was also evaluated. A significant difference in mean was observed when the concentration of henna powder was 1% and 2.5% with the p-values 0.002 and 0.001 respectively.

The mean difference, in the number of live *C. albicans*, between the two methods (Slide count and direct culture test) was −140757122 and difference between the means, obtained from two different methods was statistically significant with p-value 0.00025. 95% confidence limits lay between −1054423691 and 772909448 (FIG. 2).

FIG. 2 depicts the Bland-Altman plot showing the differences in average *Candida* colony counts in two methods. The bias is the average difference; the closer to zero, the more concordant the method. The upper and lower limits of agreement (LOA) represent bias +/−1.5 SD of the bias. The upper and lower LOA for agar dilution method and counting chamber in this experiment are (−4.4, 1.5).

TABLE 1

Effect of different concentrations of Henna on *Candida Albicans*.

| Group | Agar dilution Mode | Log Reduction in *Candida* | P-value | Counting chamber Mode | Log Reduction in *Candida* | P-value |
|---|---|---|---|---|---|---|
| A | $5 \times 10^6$ | — | — | $2 \times 10^6$ | — | — |
| B 1% | $2 \times 10^6$ | 6.5 | 0.0001* | $1 \times 10^6$ | 6 | 0.001* |
| C 2.5% | $5 \times 10^5$ | 6.7 | 0.2 | $7 \times 10^5$ | 6.1 | 0.1 |
| D 5% | $4 \times 10^6$ | 6 | 0.6667 | $2 \times 10^6$ | NA | NA |
| E 7.5% | $1 \times 10^5$ | 6.7 | 0.0001* | $1.5 \times 10^5$ | 6.3 | 0.1 |
| F 10% | $1 \times 10^4$ | 6.7 | 0.001* | $4 \times 10^4$ | 6.3 | 0.01* |

*Statistically significant at 0.05 level of significance

One purpose of this study was to measure the antifungal effect of henna extracts, in treatment and prevention of denture stomatitis for complete denture wearers. It was found that henna powder has an antifungal effect on the acrylic resin mimicking the material of a complete denture.

The present exemplary study indicated a significant difference in reducing the number of *C. albicans* was with 1% and 10% concentration of henna using both methods of evaluating. The results indicated that henna can be effective in producing antimicrobial environment against *C. albicans*.

As shown in Table 1, initial screening indicates that Henna extracts can be potential antifungal compounds to be developed further with log reduction ranging between 6-6.7 in both methods used. However, various levels of efficacy were shown by different concentrations of henna as evaluated by each method. Of note, at 5% henna the effect was suboptimal, even lower than that of lower concentrations of the henna (1% & 2.5%). This can be explained by either the coincidence of several tubes showing no growth of *candida* at all which might have reduced the accuracy of the overall estimate of colony counts at this concentration as a random error, or it could be due to reduced henna activity at this level due to kinetics considerations that are difficult to explain at early screening of a compound. Some antimicrobials are known to require a particular concentration ratio with the organism as described by the Eagle effect. Relevant pharmacokinetics data are important in order to test this hypothesis in future experimental work.

When screening a novel product, accurate but non-labour intensive techniques are desired. In this study, the counting chamber method performed well in concordance to the reference agar dilution method and gave similar log reductions with robustness and good agreement in the Bland-Altman plot (FIG. 2). Although similar in principle to the agar dilution, its advantages include practicality, ease and speed compared to agar dilution method. This study compared the counting chamber and the results shown in Table 1 illustrate comparable log reduction in cell counts, although the statistical significance was different at 7.5% henna concentration (Table 1).

The invention claimed is:

1. A denture comprising:
   a first antimicrobial ingredient, wherein the first antimicrobial ingredient is a henna powder or a henna extract, each of which comes from pulverized henna leaves and comprises at least one compound selected from the group consisting of lawsone, tannic acid, and 2-methoxy-1,4-napthoquinone;
   a denture fabrication material; and
   a biocompatible gel which is a hydrogel or a polymer gel that is a coating on the denture, integrated into the denture, or both;
   wherein the first antimicrobial ingredient covers the surface of the denture fabrication material and extends into the interior of the denture fabrication material.

2. The denture of claim 1, wherein the denture fabrication material comprises a cured acrylic resin which is poly (methyl methacrylate).

3. The denture of claim 1, wherein the denture fabrication material comprises a cured acrylic resin which is poly(ethyl methacrylate), poly(butyl methacrylate), or mixtures thereof.

4. The denture of claim 1, wherein the denture comprises 0.1% to 20% w/w of a total weight of the first antimicrobial ingredient relative to a total weight of the denture.

5. A denture, comprising
   a first antimicrobial ingredient, wherein the first antimicrobial ingredient is a henna powder or a henna extract, each of which comes from pulverized henna leaves and comprises at least one compound selected from the group consisting of lawsone, tannic acid, and 2-methoxy-1,4-napthoquinone;
   a denture fabrication material; and
   an odor neutralizer comprising two or more aldehydes selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, bucinal, thiophene carboxaldehyde, trans-4-decenal, trans trans 2,4-nonadienal, and undecyl aldehyde;
   wherein the first antimicrobial ingredient covers the surface of the denture fabrication material and extends into the interior of the denture fabrication material.

6. A denture comprising:
   a first antimicrobial ingredient, wherein the first antimicrobial ingredient is a henna powder or a henna extract, each of which comes from pulverized henna leaves and comprises at least one compound selected from the group consisting of lawsone, tannic acid, and 2-methoxy-1,4-napthoquinone;
a second antimicrobial ingredient;
a denture fabrication material; and
a biocompatible gel which is a hydrogel or a polymer gel that is a coating on the denture, integrated into the denture, or both;
wherein the first antimicrobial ingredient, the second antimicrobial ingredient, or both coat the surface of the denture fabrication material and extend into the interior of the denture fabrication material.

7. The denture of claim 6, wherein the second antimicrobial ingredient is a silver nanoparticle, a titanium dioxide particle, a silicon compound or an essential oil.

8. The denture of claim 7, wherein the second antimicrobial ingredient is the silver nanoparticle, and the silver nanoparticle has an average diameter of 40 nm to 80 nm.

9. The denture of claim 7, wherein the second antimicrobial ingredient is the titanium dioxide particle, and the titanium dioxide particle has an average diameter of 40 nm to 160 nm.

10. The denture of claim 7, wherein the second antimicrobial ingredient is the essential oil, and the essential oil is at least one selected from the group consisting of lemongrass oil, peppermint oil, neem oil, orange oil, palmarosa oil, and patchouli oil.

11. The denture of claim 6, wherein the denture comprises 0.1% to 25% w/w of a total weight of the first antimicrobial ingredient and the second antimicrobial ingredient relative to a total weight of the denture.

12. The denture of claim 6, further comprising a third antimicrobial ingredient selected from the group consisting of 3-alkyl-2-hydroxy-1,4-napthoquinone, 2-amino-1,4-napthoquinone, and 3-aminophenyl-2-hydroxy-1,4-napthoquinone.

13. The denture of claim 12, wherein the denture comprises 0.1%-5% w/w of the third antimicrobial ingredient relative to a total weight of the denture.

14. The denture of claim 6, further comprising an odor neutralizer comprising two or more aldehydes selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, bucinal, thiophene carboxaldehyde, trans-4-decenal, trans trans 2,4-nonadienal, and undecyl aldehyde.

15. The denture of claim 6, wherein the denture fabrication material comprises a cured acrylic resin which is poly(methyl methacrylate).

16. The denture of claim 6, wherein the denture fabrication material comprises a cured acrylic resin which is poly(ethyl methacrylate), poly(butyl methacrylate), or mixtures thereof.

* * * * *